United States Patent [19]

Deprez et al.

[11] 4,444,645

[45] Apr. 24, 1984

[54] MEASURING APPARATUS FOR THE ANALYTICAL DETERMINATION OF A GAS PARTIAL PRESSURE

[75] Inventors: Jacques Deprez, Frechen; Eckard Drope; Peter Greif, both of Cologne; Gabriele Soth-Haas, Leverkusen, all of Fed. Rep. of Germany

[73] Assignee: Bayer Aktiengesellschaft, Leverkusen, Fed. Rep. of Germany

[21] Appl. No.: 397,618

[22] Filed: Jul. 12, 1982

[30] Foreign Application Priority Data

Jul. 28, 1981 [DE] Fed. Rep. of Germany ....... 3129680

[51] Int. Cl.$^3$ ............................................. G01N 27/46
[52] U.S. Cl. .................................... 204/409; 204/1 T; 204/400; 204/431; 204/432
[58] Field of Search ............... 204/1 T, 1 F, 400, 409, 204/431, 432

[56] References Cited

U.S. PATENT DOCUMENTS

| | | | |
|---|---|---|---|
| 3,997,420 | 12/1976 | Buzza | 204/420 |
| 4,029,563 | 6/1977 | Binder et al. | 204/1 F |
| 4,049,503 | 9/1977 | Becker et al. | 204/1 F |
| 4,141,800 | 2/1979 | Breuer et al. | 204/1 F |
| 4,319,966 | 3/1982 | Carlson et al. | 204/1 F |

Primary Examiner—T. Tung
Attorney, Agent, or Firm—Sprung, Horn, Kramer & Woods

[57] ABSTRACT

The measuring apparatus is based on an electrochemical sensor with a hollow chamber connected upstream through which the gas to be measured diffuses to the sensor surface. A pump for introducing a rinsing gas is connected to the hollow chamber. Moreover, the rinsing gas connection is connected to a test gas source which produces a known concentration of the component to be measured. The function of the sensor may be controlled by connecting the test gas source. The accuracy of the measured values and thus the reliability of the measuring apparatus may be substantially improved by these measures.

6 Claims, 6 Drawing Figures

MEASURING APPARATUS FOR THE ANALYTICAL DETERMINATION OF A GAS PARTIAL PRESSURE

BACKGROUND OF THE INVENTION

This invention relates to a measuring apparatus having a widened measuring scope for the analytical determination of a gas partial pressure. The apparatus is based on an electrochemical sensor with a hollow chamber through which the gas diffuses to the sensor surface.

Sensors of this type are described, for example in U.S. Pat. Nos. 4,049,261 and 4,141,800. They are based on the principle that the molecules of the gas to be measured entering into the hollow chamber by diffusion and impinging on the sensor surface are detected and counted due to a physical reaction on the sensor surface. The reaction takes place on a three-phase boundary of electrolyte/electrode/gas chamber. Due to the nature of the measuring effect, the measuring range of such sensors is restricted at both higher and lower levels. The lower limit, i.e. the detection limit, is predetermined by the zero-point level. The upper limit is set by the capacity to remove the molecules of the gas to be measured on the three-phase boundary, since when subsequent supply of the reactants or the regeneration of the electrolyte no longer keeps up with the arrival of the molecules of the gas to be measured, non-linearity and a clear deterioration in the time characteristic occurs. In order to also be able to use electro-chemical sensors for higher concentrations, the diffusion flow impinging on the sensor surface must be restricted. For this purpose, suitable inlet diaphragms are connected upstream of the diffusion chamber (see European Offenlegungsschrift No. 16 423). However, the measuring range is fixed permanently by the dimensioning of the inlet diaphragm. When a transition is made to another concentration range, the diaphragm head has to be exchanged manually.

Gas analysis devices are nowadays also being used to an increasing extent in industrial practice for guaranteeing safety at work. Particularly high demands must be made on the reliability of these devices when it is a matter of detecting and measuring dangerous working materials. The measuring apparatus must give a rapid and reliable warning when dangerous concentrations occur in the air. Such measuring apparatus are typically installed in stationary installations, or are given as portable devices to persons who are at risk. The stationary measuring apparatus take samples of air from one or more locations, which samples are passed on to the analytical determination means through suction lines or by free diffusion. The analysis device is thus frequently installed in a rather inaccessible location, so that when assessing the situation, the operating staff has to rely completely on the test signal which is registered on a recording instrument. The same applies correspondingly to rooms which are rarely visited. Before a person enters such a room, he must be able to assure himself in each case that a harmful concentration of gas is not present therein.

Thus, the specific requirements of such stationary measuring apparatus may be characterized as follows:

1. A rapid response time, both for an increase and for a decrease in concentration.
2. No impairment of the measuring behavior caused by higher concentration peaks of the gas to be measured.
3. A reliable detection of the operational or functional condition of the measuring apparatus, in particular when there is a sensitivity loss of the sensor.
4. Low maintenance expenditure, particularly in remote sample-taking locations or in distant analysis devices.
5. An effective prevention of manipulation by the operating staff (avoidance of erroneous adjustments).

The demand for high sensitivity and a favorable time behavior may be effectively met using electrochemical sensors. However, the weakness of these sensors lies in their low overload capacity. High concentrations frequently result in a long regeneration time, and consequently, in a loss of sensitivity and in an impaired time behavior. The demand for reliable defection of the functional condition is partly met in modern analysis devices by expensive and complex monitoring units which are provided as supplementary devices.

SUMMARY OF THE INVENTION

The present invention is based on the object of providing a gas analysis apparatus having a widened measuring scope based on an electrochemical measuring cell of predetermined sensitivity and predetermined time behavior which, without overloading, may be exposed to high concentrations of gas, and the perfect operation of which may be controlled remotely at any time without requiring complex supplementary apparatus.

This object is achieved according to the present invention, starting from the electrochemical sensor which has already been described, in that the hollow chamber upstream of the sensor has a connection with a pump for introducing a rinsing gas, and a test gas source having a known concentration of the component to be measured may be connected to the rinsing gas connection for the functional control of the sensor. The rinsing gas is preferably provided in that during the measuring operation, the pump communicates on the suction side with the atmosphere to be examined via a filter absorbing the component to be measured. The rinsing gas which is free from the component to be measured and is introduced into the hollow chamber counteracts the diffusion flow of this component, so that the gas concentration impinging on the sensor surface is reduced.

Measures involving technical switching automatically enable the flow of rinsing gas to be increased when the concentration of gas increases. For this purpose, the sensor with a measuring amplifier connected downstream is connected in the manner of a feedback to the pump motor as a control loop, in which the conveying capacity of the pump is increased as the sensor signal increases. In this case, it may be provided that the control only starts above a threshold value of the sensor signal. In this arrangement, the measured value for high gas concentrations may be traced back to a current or voltage measurement at the pump motor.

This invention provides an ensured quality of the measured values in the sense of improved reliability. On the one hand, harmful overloads are avoided at high gas concentrations by charging the sensor with rinsing gas. On the other hand, the function of the sensor may be tested by a temporary connection of the test gas source which produces a known concentration of the component to be measured. The test may either be carried out manually (by actuating a switch) or fully automatically at regular time intervals. The measuring head with the sensor then only needs to be serviced when a negative result of the function test is reported to the control station.

The present invention will now be explained in more detail in the following with reference to embodiments and drawings, in which:

DETAILED DESCRIPTION OF THE INVENTION

Figure 1:
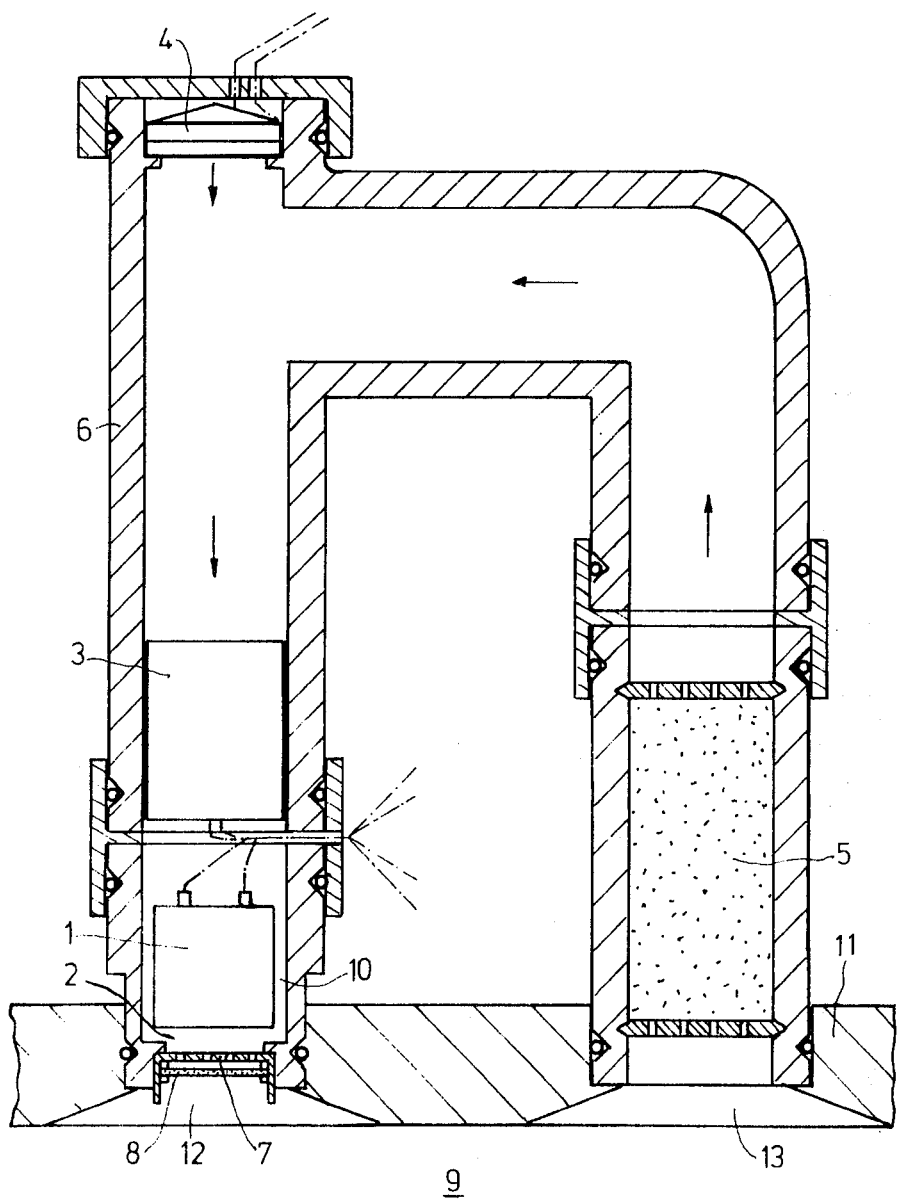
FIG. 1 illustrates an embodiment of the measuring apparatus according to the present invention, in which the rinsing gas is led past the sensor.

The essential components of the measuring head illustrated in FIG. 1 are an electrochemical sensor 1 with a hollow chamber 2 connected upstream, a ventilator as a pump 3, a generator cell 4 and an air filter 5. The measuring cell 1 is to be positioned in a pipeline 6 which communicates on the one hand with the atmosphere 9 to be tested via a diaphragm 7 and a dust filter 8 and on the other hand to the atmosphere via an air filter 5. The gas to be measured, i.e. hydrogen sulphide in air, diffuses through the dust filter 8, the diaphragm 7 and the adjacent hollow chamber 2, on to the sensor surface of the measuring cell 1 and produces a corresponding electrical signal. Suitable measuring cells are described, for example in German Offenlegungsschrift Nos. 2,436,261 and 2,621,676. A small ventilator, for example, may be used as the pump 3. The generator cell 4 is used for producing a test gas having a known concentration of the component to be measured. It comprises, for example an electrolysis cell through which a surge of current is sent. In this manner, a concentration surge of the test gas is produced for a short time. A detailed description of such generator cells is provided in German Pat. No. 2,621,677.

The operation of the measuring head is based on the fact that the ventilator 3 sucks in rinsing gas from the atmosphere 9 via the line 6, which gas is returned into the atmosphere through the annular channel 10 between the measuring cell 1, the pipeline 6 and the hollow chamber 2. The granulate filter 5 ensures that the rinsing gas if freed from the component to be measured. Thus, the ventilator 3 Produces a counterflow in the diffusion cavity 2 which weakens the diffusion flow of the measuring component in a definite manner and thus reduces the sensitivity of the measuring apparatus. By adjusting the ventilator speed via the electric voltage which is applied, the measuring range may be varied within wide limits and may be adapted to the particular measuring problem.

In order to effect the sensor functional control, the test gas generator 4 merely needs to be activated in the above-described manner. The rinsing gas which has been sucked in is then charged with the component to be measured during the connection time of the test gas generator. As a result of this, a signal which must lie between predetermined limits is produced at the sensor 1. Instead of the generator cell 4, a reservoir, which is filled with the test gas and is connected to the line 6 for a short time via a valve, could naturally also be Provided.

As may be seen from FIG. 1, the components 1 to 5 of the measuring apparatus are integrated in a compact measuring head, the base plate 11 of which contains the openings 12, 13 for the entry of the gas to be measured and the rinsing gas respectively.

Figure 2:
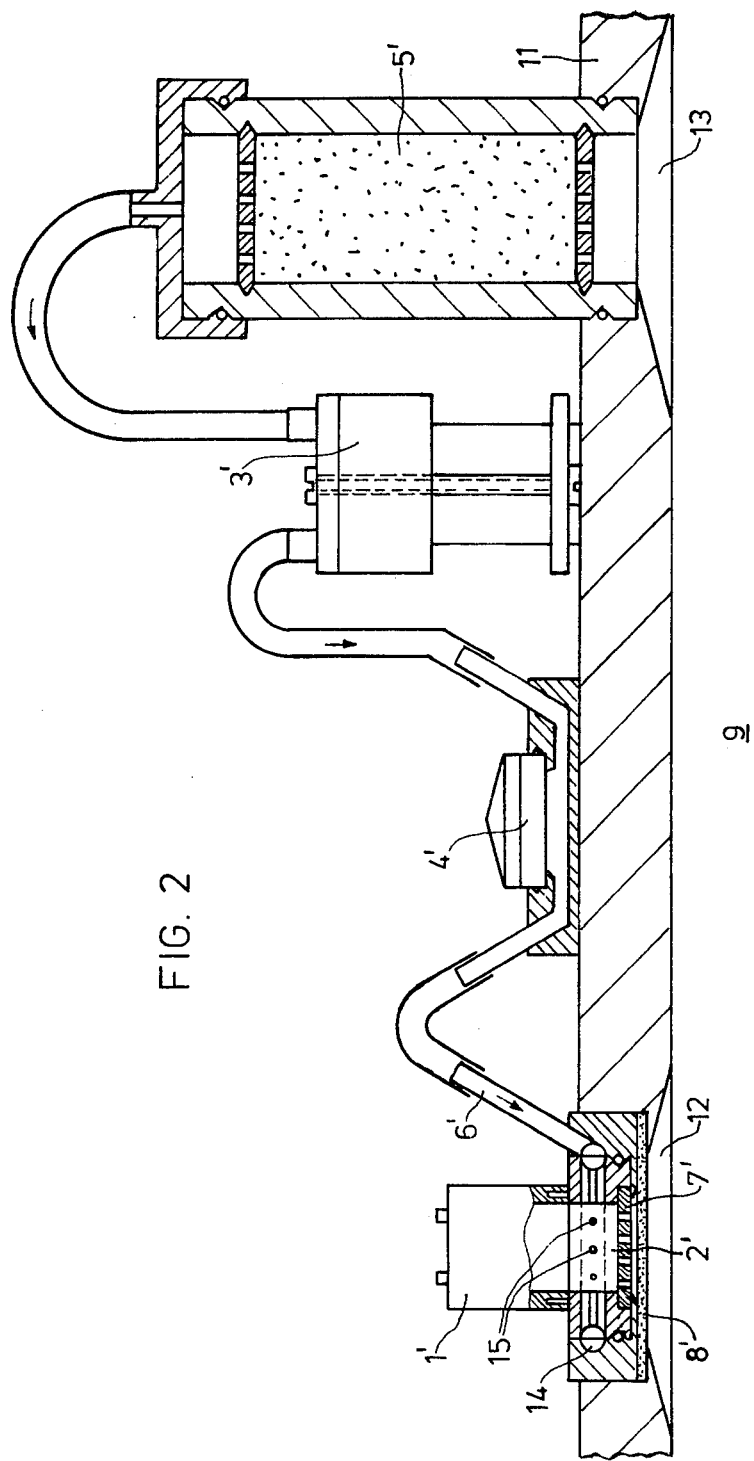
FIG. 2 illustrates an embodiment in which the rinsing gas is supplied laterally to the diffusion hollow chamber.

The arrangement according to FIG. 2 is an alternative embodiment of the measuring apparatus. In this case, the rinsing gas connection 6 discharges laterally into the cavity 2' upstream of the sensor 1'. The connection is designed as an annular pipe 14 having bores 15 through which the rinsing gas flows into the cavity and from there, flows out through the diaphragm 7' and the dust filter 8'. In this manner, a regular distribution and mixing of the rinsing gas with the measuring gas is obtained in the cavity 2.

In FIG. 2, the test gas generator 4' for the functional control of the electrochemical sensor 1' is directly connected into the rinsing gas supply line. The pump 3' which sucks in the rinsing gas through the inlet opening 13 via the absorption filter 5', as in the embodiment according to FIG. 1, is a standard miniature rotary piston pump. Compared to the ventilator in the embodiment according to FIG. 1, it has a higher suction power, so that a greater flow of rinsing gas may be produced. As a result of this measure, even higher concentrations are admissible. In addition to the enlarged measuring scope, the measuring apparatus according to FIG. 2 also has a more favorable (faster) time behavior.

Figure 3:
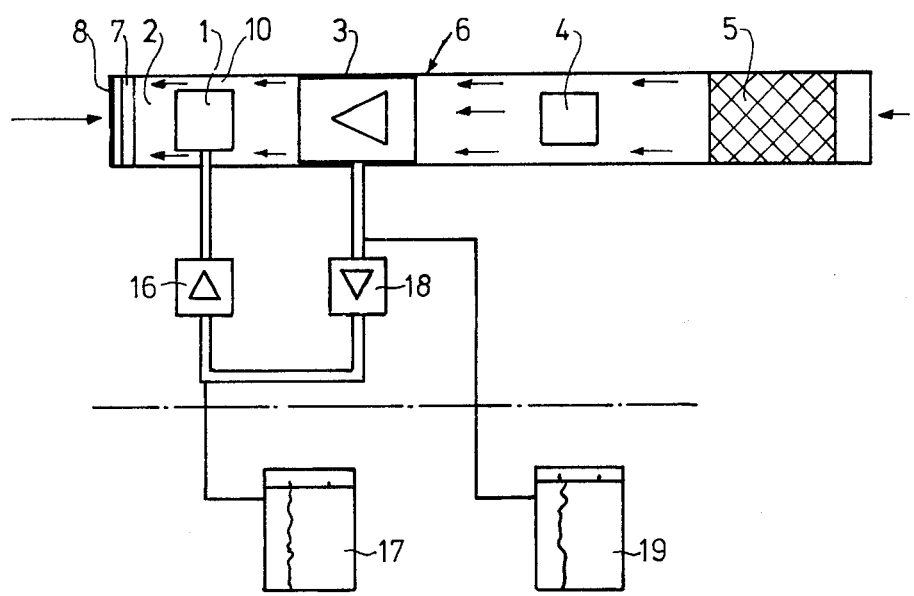
FIG. 3 is a block diagram of the measuring apparatus.

FIG. 3 schematically illustrates the electronic signal processing of the measuring apparatus. Assuming that the electrochemical sensor is terminated with low resistance, it produces a current which is proportional to the concentration of gas to be measured impinging on the sensor surface. This current is amplified in a measuring amplifier 16 and is registered by the recording device 17. Moreover, the amplified test signal is supplied to a power amplifier 18 which feeds the pump 3 in the rinsing gas line 6. If the test signal exceeds an adjustable limiting value (threshold switch), then the pump 3 is started and it produces a flow of rinsing gas which, as described above, counteracts the measuring effect. The speed of the pump 3 and thus the conveying capacity thereof increases according to the increasing test signal. The sensor 1 (measuring sensor), together with the amplifiers 16 and 18 and the pump 3 (regulating member) thus form a control loop. During the control operation (test signal greater than the threshold voltage), the pump voltage may advantageously be used for the production of the measured value. The recording device 19 is provided for this purpose.

Figure 4:
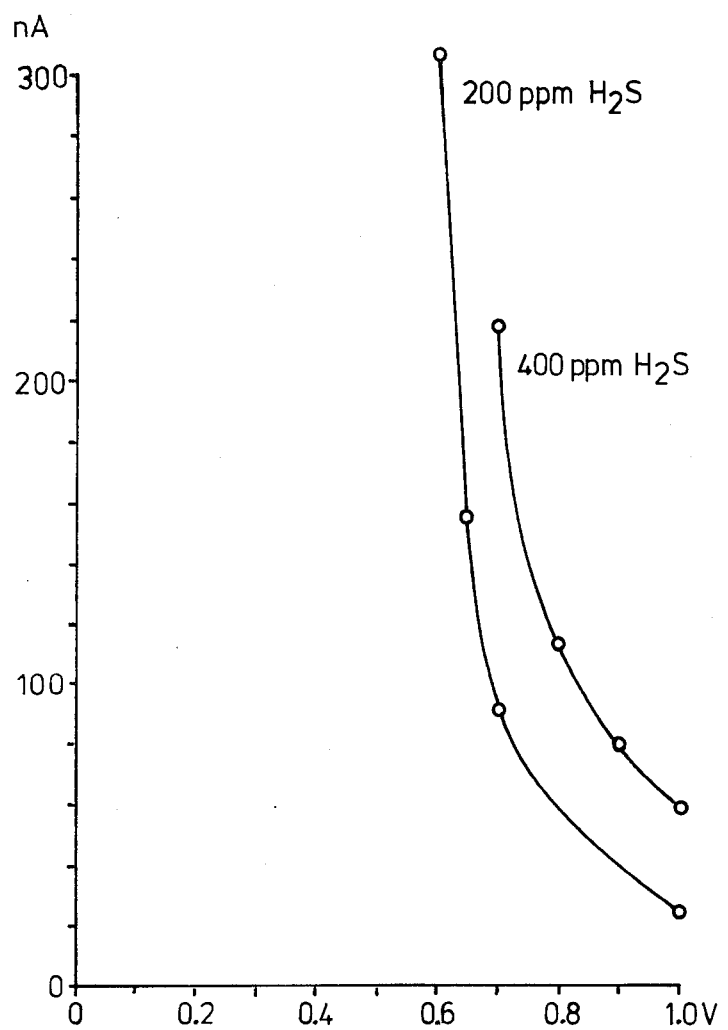
FIGS. 4 to 6 are different diagrams to explain the measuring cell flow characteristic.

In FIG. 4, the test signal (cell current) has been plotted as a function of the pump voltage with constant gassing (200 and 400 ppm of hydrogen sulphide). In this case, the pump voltage was varied externally and was not subsequently automatically adjusted as in FIG. 3. It is seen that the cell current considerably decreases with an increasing pump voltage and with a correspondingly increasing speed of the pump. Thus, the greater the flow of rinsing gas produced by the pump 3, the more the diffusion flow of the measuring component, which impinges on the sensor surface and is critical to the measuring effect, is reduced as a result of this, the sensitivity of the measuring apparatus is drastically reduced.

Figure 5:
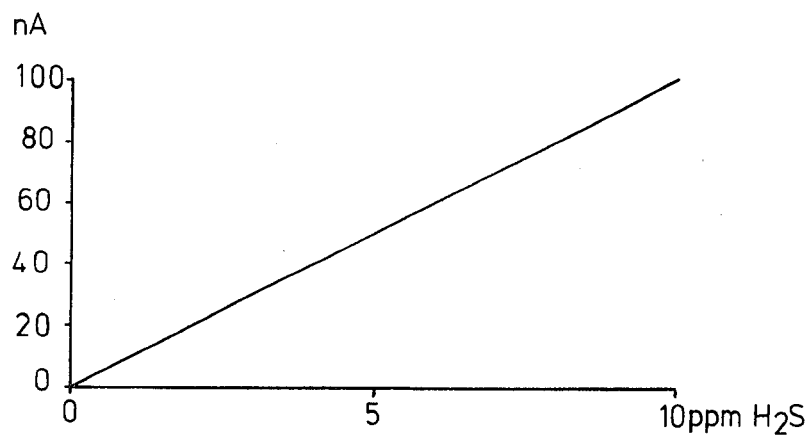
Figure 6:
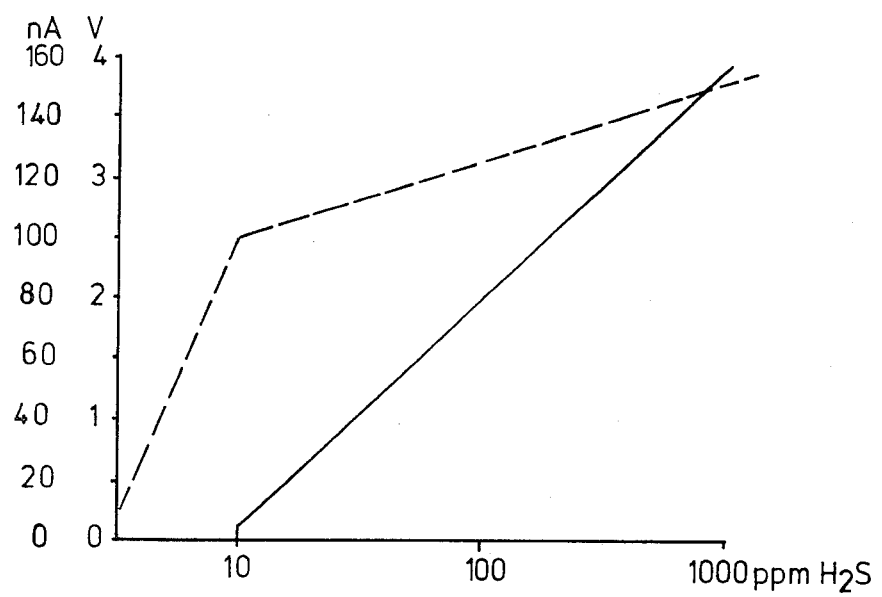

The graphs in FIGS. 5 and 6 were plotted using the connections according to FIG. 3. The gas to be measured again consisted of air having a low partial pressure of hydrogen sulphide. The dependence of the measurable variable on the concentration of hydrogen sulphide was tested. FIG. 5 illustrates the linear increase of the cell current in the region of very low $H_2S$ concentrations (from 0 to 10 ppm). The threshold voltage at which the pump 3 starts to operate and produces rinsing gas is a few tenths of a volt, corresponding to a cell current of 100 nA. The relevant $H_2S$ concentration is 10 ppm. The control commences at this value. The pump 3 starts to operate and blows rinsing gas into the diffusion hollow chamber 2 upstream of the sensor 1. This behaviour is illustrated in FIG. 6. In this case, the $H_2S$ concentration is plotted on a logarithmic scale (from 10 to 1000 ppm) as the abscissa and the measuring cell current and the voltage at the pump motor are plotted as the ordinate. The dashed line represents the variation of the measuring cell current and the full line represents the variation of the pump voltage. The first increase in the measuring cell current up to 100 nA corresponds to FIG. 5. The line bends sharply at 10 ppm. The measuring cell current then only continues to increase gently due to the increasing flow of rinsing gas, with an increasing concentration. The pump voltage (full line) is a direct measurement of the conveying capacity. Conversely, it is also possible to say that a specific value of the pump voltage is adjusted at each predetermined $H_2S$ concentration in the range of from 10 to 1,000 ppm due to the regulating effect. Thus, the pump voltage may be used as a measurable variable for the concentration in this range. The threshold value for commencement of the control must be chosen to be low enough in each case for the sensor to be still not overloaded in the starting condition (from 0 to 10 ppm; see FIG. 5). By using a microprocessor in the control loop, any desired control characteristic may be produced electronically. In this manner, the control behaviour of the measuring apparatus may be adapted optimally in each case to the measuring problem.

The widening of the measuring scope of the gas analysis apparatus may be readily seen from FIGS. 5 and 6. Without weakening the concentration of gas to be measured by the rinsing effect, the electrochemical measuring cells based on a gel electrolyte which are used would be irreversibly overloaded in the region of from 10 to 100 ppm. The test gas generator which may be switched in as desired and is connected to the rinsing gas line allows a regular functional control of the measuring apparatus. Both measures, the introduction of rinsing gas at high concentrations and the test gas generator for functional control, thus contribute to a decisive improvement in reliability. The new measuring apparatus has proved to be successful as a remote measuring head in stationary installations for monitoring air in a room. Another important use of the apparatus includes searching for leaks in gas-conducting pipelines under excess pressure. For this purpose, a specific sensor for the gas in the pipeline must be installed in the measuring apparatus. In the case of leak searching devices, a detector characteristic is generally strived for, as is illustrated in FIG. 6 for the measuring cell current.

We claim:

1. In a measuring apparatus for the analytical determination of a gas component, having an electrochemical sensor for producing an electrical signal representative of the concentration of a gas component, a cavity adjacent to the sensor surface and through which the gas diffuses to the sensor surface, the improvement comprising: pumping means connected to the cavity for flowing a given gas therein which is free of the gas component to be sensed, and means for controlling the pumping means in response to the electrical signal produced by the sensor to reduce the concentration of the gas component at the sensor surface upon an indication by the electrical signal of an increase in concentration of the gas component.

2. The measuring apparatus according to claim 1, wherein the pumping means communicates on the suction side thereof with the atmosphere to be examined via a filter absorbing the gas component to be measured.

3. The measuring apparatus according to claim 1, wherein the controlling means includes a measuring amplifier connected between the sensor and the pumping means for increasing the conveying capacity of the pumping means when the sensor signal increases.

4. The measuring apparatus according to claim 3, wherein the controlling means only operates above a threshold value of the sensor signal.

5. The measuring apparatus according to claim 3, wherein the pumping means includes a pump motor and further comprising means for determining the measured value for the concentration of the gas component in accordance with the current or voltage at the pump motor.

6. The measuring apparatus according to claim 1, further comprising a test gas source connectable for temporarily injecting a known concentration of the gas component to be measured into the flow of the given gas.

* * * * *